United States Patent
Shimizu et al.

(10) Patent No.: US 10,278,625 B2
(45) Date of Patent: May 7, 2019

(54) BLOOD MEASURING APPARATUS USING SPECTROSCOPE

(71) Applicant: ARKRAY, Inc., Kyoto (JP)

(72) Inventors: Takeshi Shimizu, Kyoto (JP); Yasuhide Kusaka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 315 days.

(21) Appl. No.: 15/288,523

(22) Filed: Oct. 7, 2016

(65) Prior Publication Data

US 2017/0119286 A1 May 4, 2017

(30) Foreign Application Priority Data

Oct. 29, 2015 (JP) .................................. 2015-212668
Oct. 5, 2016 (JP) .................................. 2016-197062

(51) Int. Cl.
*A61B 5/00* (2006.01)
*A61B 5/145* (2006.01)
*A61B 5/1455* (2006.01)

(52) U.S. Cl.
CPC .......... *A61B 5/1455* (2013.01); *A61B 5/0075* (2013.01); *A61B 5/14532* (2013.01);
(Continued)

(58) Field of Classification Search
CPC ..... A61B 5/1455; A61B 5/489; A61B 5/0075; A61B 5/14532; A61B 5/14552; A61B 5/0064; A61B 5/14546; A61B 5/145
See application file for complete search history.

(56) References Cited

U.S. PATENT DOCUMENTS

2005/0288564 A1 12/2005 Iuliano
2006/0181791 A1 8/2006 Van Beek et al.
(Continued)

FOREIGN PATENT DOCUMENTS

WO 2014/178199 A1 11/2014

OTHER PUBLICATIONS

The extended European search report issued by the European Patent Office dated Jun. 20, 2017, which corresponds to European Patent Application No. 16193470.8-1657 and is related to U.S. Appl. No. 15/288,523.
(Continued)

*Primary Examiner* — Eric F Winakur
*Assistant Examiner* — Abid A Mustansir
(74) *Attorney, Agent, or Firm* — Studebaker & Brackett PC (57) ABSTRACT

Provided is a blood measuring apparatus including: a spectroscope; an optical system configured to irradiate a living body with excitation light from a light source, and to guide, to the spectroscope, Raman scattered light from the living body; a control unit configured to adjust an irradiation position at which the living body is irradiated with the excitation light by the optical system; and a detector configured to detect a spectrum of the Raman scattered light using light of each wavelength dispersed by the spectroscope. A plurality of the spectra detected by the detector are integrated, and numerical value information regarding a substance included in blood of the living body is measured based on an integration result, and the control unit adjusts the irradiation position such that the plurality of spectra are detected at changed positions.

7 Claims, 7 Drawing Sheets

(52) U.S. Cl.
CPC ............ *A61B 5/489* (2013.01); *A61B 5/0064* (2013.01); *A61B 5/145* (2013.01); *A61B 5/14546* (2013.01); *A61B 5/14552* (2013.01)

(56) References Cited

U.S. PATENT DOCUMENTS

| | | |
|---|---|---|
| 2010/0309466 A1 | 12/2010 | Lucassen et al. |
| 2014/0204378 A1* | 7/2014 | Day .................. G01J 3/2823 356/326 |
| 2016/0157757 A1 | 6/2016 | Murthy |

OTHER PUBLICATIONS

Shao et al.; In Vivo Blood Glucose Quantification Using Raman Spectroscopy; PLOS ONE; Oct. 2012; pp. 1-6; vol. 7; Issue 10; e48127.

The partial European search report issued by the European Patent Office dated Mar. 17, 2017, which corresponds to European Patent Application No. 16193470.8-1657, including Information on Search Strategy, and is related to U.S. Appl. No. 15/288,523.

\* cited by examiner

BLOOD MEASURING APPARATUS USING SPECTROSCOPE

CROSS-REFERENCE TO RELATED APPLICATION

This application is based upon and claims the benefit of priority from Japanese patent application No. 2015-212668, filed on Oct. 29, 2015, and Japanese patent application No. 2016-197062, filed on Oct. 5, 2016, the disclosure of which are incorporated herein in its entirety by reference.

BACKGROUND OF THE INVENTION

Field of the Invention

The present invention relates to a blood measuring apparatus, and in particular relates to a blood measuring apparatus that uses Raman spectroscopy.

Description of Related Art

Methods for measuring the concentration of each component in blood in a non-invasive manner have been developed. For example, Non-patent Document 1 (Jingwei Shao and 6 others, "In Vivo Blood Glucose Quantification Using Raman Spectroscopy", PLOS ONE, Vol. 7, No. 10, e48127, October 2012) discloses a method for acquiring a Raman spectrum by focusing laser light in a blood vessel within a skin, and measuring the glucose concentration of the blood based on the intensity ratio between the glucose peak and the hemoglobin peak in the acquired Raman spectrum.

Also, Patent Document 1 (WO 2014/178199) discloses a monitor for monitoring the internal state of a living body from a living body surface, the monitor including: a probe that is attached to the living body surface and includes an observation window; a unit for irradiating, with a laser, at least a portion of an observation region of the living body surface accessed via the observation window; a unit for detecting scattered light caused by the laser irradiation from each of a plurality of observation spots formed intermittently so as to disperse two-dimensionally over the observation region or formed continuously so as to scan over the observation region; a unit for selecting, from the plurality of observation spots, a first observation spot determined to provide scattered light that includes information regarding a target portion inside the living body, based on scattered light acquired from the plurality of observation spots; and a unit for acquiring an optical spectrum of at least one component from the first observation spot or surrounding observation spots, and outputting first information indicating the internal state of the living body based on the intensity of the spectrum.

SUMMARY OF THE INVENTION

There is a desire for a technique that makes it possible to favorably measure blood beyond these techniques described in Non-patent Document 1 and Patent Document 1.

This invention has been made in order to solve the above-described issue, and an object of this invention is to provide a blood measuring apparatus capable of favorably measuring blood.

(1) A blood measuring apparatus according to an aspect of this invention includes: a spectroscope; an optical system configured to irradiate a living body with excitation light from a light source, and to guide, to the spectroscope, Raman scattered light from the living body; a control unit configured to adjust an irradiation position at which the living body is irradiated with the excitation light by the optical system; and a detector configured to detect a spectrum of the Raman scattered light using light of each wavelength dispersed by the spectroscope, wherein a plurality of the spectra detected by the detector are integrated, and numerical value information regarding a substance included in blood of the living body is measured based on an integration result, and the control unit adjusts the irradiation position such that the plurality of spectra are detected at changed positions.

(2) Preferably, the blood measuring apparatus further includes: a determination unit configured to perform determination processing for determining, based on the spectrum detected by the detector, whether or not the irradiation position is a blood vessel position of the living body, wherein the determination unit performs the determination processing a plurality of times, and the control unit changes the irradiation position after the determination processing is performed.

(3) More preferably, the blood measuring apparatus further includes: a calculation unit configured to integrate the plurality of spectra detected by the detector, wherein the calculation unit excludes, as an integration target, the spectrum corresponding to the irradiation position determined in the determination processing not to be the blood vessel position.

(4) Preferably, a time during which the same irradiation position is continuously irradiated with the excitation light is limited, and a setting of the time can be changed.

(5) A blood measuring apparatus according to another aspect of this invention includes: a spectroscope; an optical system configured to irradiate a living body with excitation light from a light source, and to guide, to the spectroscope, Raman scattered light from the living body; a control unit configured to adjust an irradiation range or an irradiation intensity of the excitation light with which the living body is irradiated by the optical system; and a detector configured to detect a spectrum of the Raman scattered light dispersed by the spectroscope, wherein a plurality of the spectra detected by the detector are integrated and numerical value information regarding a substance included in blood of the living body is measured based on an integration result, the control unit performs, after the spectrum is detected by the detector, adjustment processing for enlarging the irradiation range and then restoring the irradiation range, or reducing the irradiation intensity and then restoring the irradiation intensity, and the detector newly detects the spectrum after the adjustment processing is performed.

(6) Preferably, the blood measuring apparatus further includes a determination unit configured to perform determination processing for determining, based on the spectrum detected by the detector, whether or not an irradiation position of the excitation light with which the living body is irradiated is a blood vessel position of the living body, wherein the control unit, in the case where it is determined in the determination processing that the irradiation position is not the blood vessel position, changes the irradiation position, and in the case where it is determined in the determination processing that the irradiation position is the blood vessel position, performs the adjustment processing.

(7) More preferably, the blood measuring apparatus further includes a calculation unit for integrating the plurality of spectra detected by the detector, wherein the calculation unit excludes, as an integration target, the spectrum corresponding to the irradiation position determined in the determination processing not to be the blood vessel position.

(8) Preferably, the living body is irradiated with the excitation light having an irradiation range of a predetermined size and an irradiation intensity of a predetermined magnitude in order to detect the spectrum, at least one of a duration for the irradiation range of a predetermined size and a duration for the irradiation intensity of a predetermined magnitude is limited, and a setting of the limited duration can be changed.

According to the present invention, blood can be favorably measured.

The foregoing and other objects, features, aspects and advantages of the present invention will become more apparent from the following detailed description of the present invention when taken in conjunction with the accompanying drawings.

DETAILED DESCRIPTION OF THE INVENTION

Embodiments of the present invention will be described below with reference to the drawings. Note that in the drawings, the same reference signs are given to the same or equivalent constituent elements and description thereof is not repeated. Moreover, at least a portion of the embodiments that will be described below may be suitably combined.

First Embodiment

Configuration of Blood Measuring Apparatus

Figure 1:
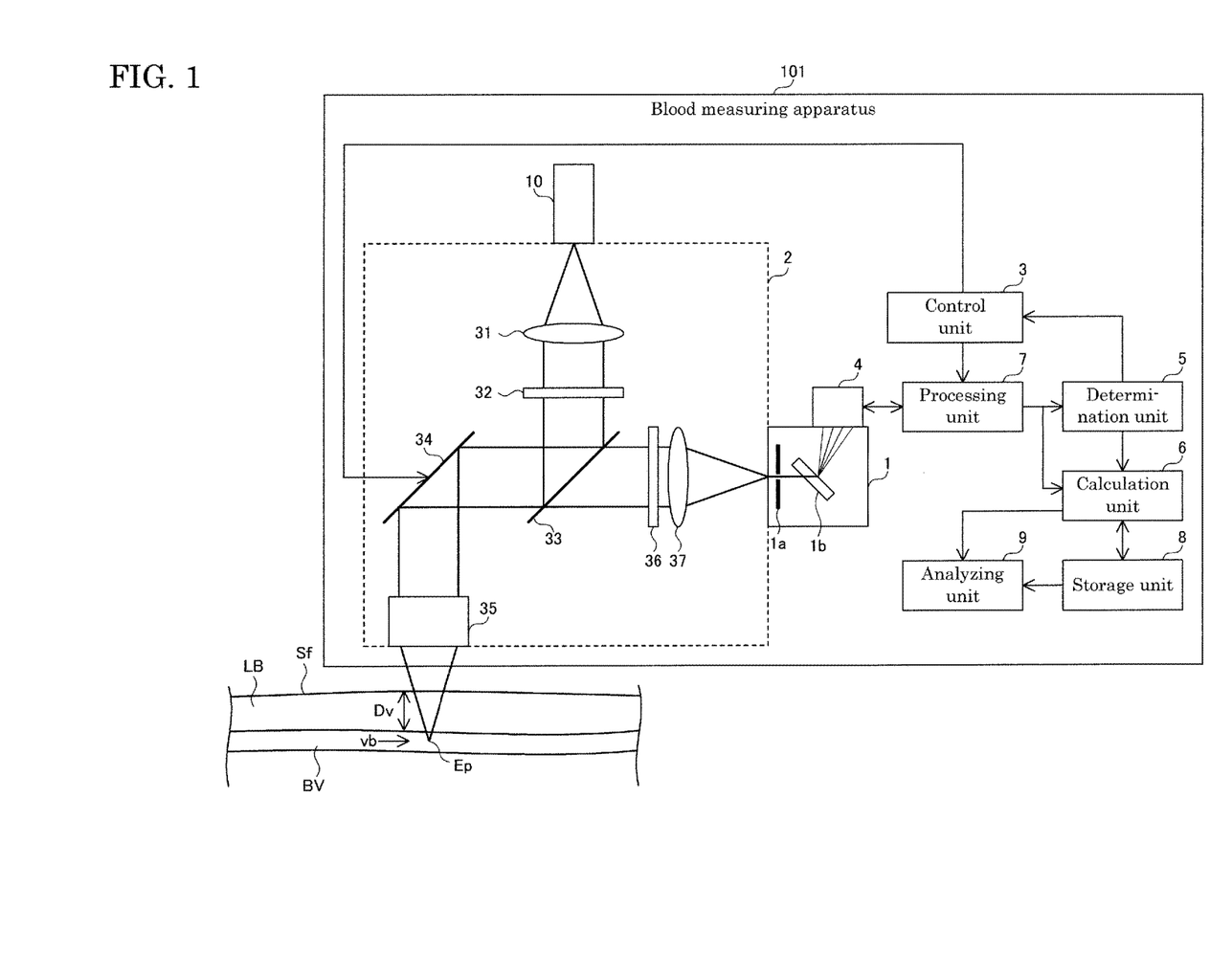
FIG. 1 is a diagram showing a configuration of a blood measuring apparatus according to a first embodiment of the present invention.

FIG. 1 is a diagram showing the configuration of a blood measuring apparatus according to a first embodiment of the present invention.

As shown in FIG. 1, a blood measuring apparatus 101 is provided with a spectroscope 1, an optical system 2, a control unit 3, a detector 4, a determination unit 5, a calculation unit 6, a processing unit 7, a storage unit 8, an analyzing unit 9 and a light source 10. The spectroscope 1 includes a slit 1a and a diffraction lattice 1b. The optical system 2 includes a collimate lens 31, a band pass filter 32, a dichroic mirror 33, a scanning mirror 34, an objective lens 35, a band pass filter 36 and a condensing lens 37.

For example, the light source 10 is a light source that emits excitation light by itself, and is specifically a laser that outputs monochrome light. Note that the light source 10 may also be an LED (Light-Emitting Diode). Also, the light source 10 may be provided outside of the blood measuring apparatus 101.

In this example, the light source 10 is a cw (continuous wave) laser, for example, and irradiates the collimate lens 31 in the optical system 2 with laser light whose power and wavelength are respectively 50 mW and 785 nm, as excitation light.

The optical system 2 irradiates a living body LB with excitation light from the light source 10, and guides Raman scattered light from the living body LB to the spectroscope 1.

More specifically, for example, the collimate lens 31 in the optical system 2 converts excitation light received from the light source 10 into substantially parallel light.

For example, the band pass filter 32 attenuates, among the wavelength components of excitation light from the collimate lens 31, wavelength components other than that at the peak in the spectrum of the excitation light, namely, the strongest peak in the laser light.

For example, excitation light that has been transmitted by the band pass filter 32 is reflected by each of the dichroic mirror 33 and the scanning mirror 34, and is incident to the objective lens 35. Here, for example, the dichroic mirror 33 reflects excitation light, while transmitting Raman scattered light, which will be described later, having a different wavelength from that of the excitation light.

The objective lens 35 focuses, on the living body LB, excitation light that has been reflected by the scanning mirror 34, for example. A position at which the excitation light is focused by the objective lens 35 in this manner is an irradiation position Ep at which the living body LB is irradiated with the excitation light by the optical system 2.

At the irradiation position Ep of excitation light, specific scattered light that is based on the excitation light is produced from substances in a living body such as blood, fat or the components contained in the blood. This scattered light includes Raman scattered light caused by Raman scattering, and Rayleigh scattered light caused by Rayleigh scattering, for example.

For example, the objective lens 35 converts, into substantially parallel light, scattered light that spreads from the irradiation position Ep of excitation light. The scanning mirror 34 reflects the substantially parallel light from the objective lens 35, for example.

The band pass filter 36 attenuates the wavelength component at the peak in the spectrum of the above excitation light, among the wavelength components of scattered light that was reflected by the scanning mirror 34 and transmitted by the dichroic mirror 33, for example.

The condensing lens 37 focuses, in the slit 1a in the spectroscope 1, scattered light that has been transmitted by the band pass filter 36, for example.

The scattered light that has passed through the slit 1a in the spectroscope 1 is diffracted by the diffraction lattice 1b and is irradiated onto the detector 4, for example.

The detector 4 detects the spectrum of Raman scattered light using light of each wave number or each wavelength dispersed by the spectroscope 1. Here, it is sufficient that the detector 4 measures light of at least two wave numbers or wavelengths.

More specifically, for example, upon receipt of a measurement instruction including an exposure duration Te from the processing unit 7, the detector 4 measures the spectrum by accumulating, for the exposure duration Te, the intensity of the scattered light for each wavelength diffracted by the diffraction lattice 1b. The detector 4 then outputs the measured spectrum to the processing unit 7, for example.

Figure 2:
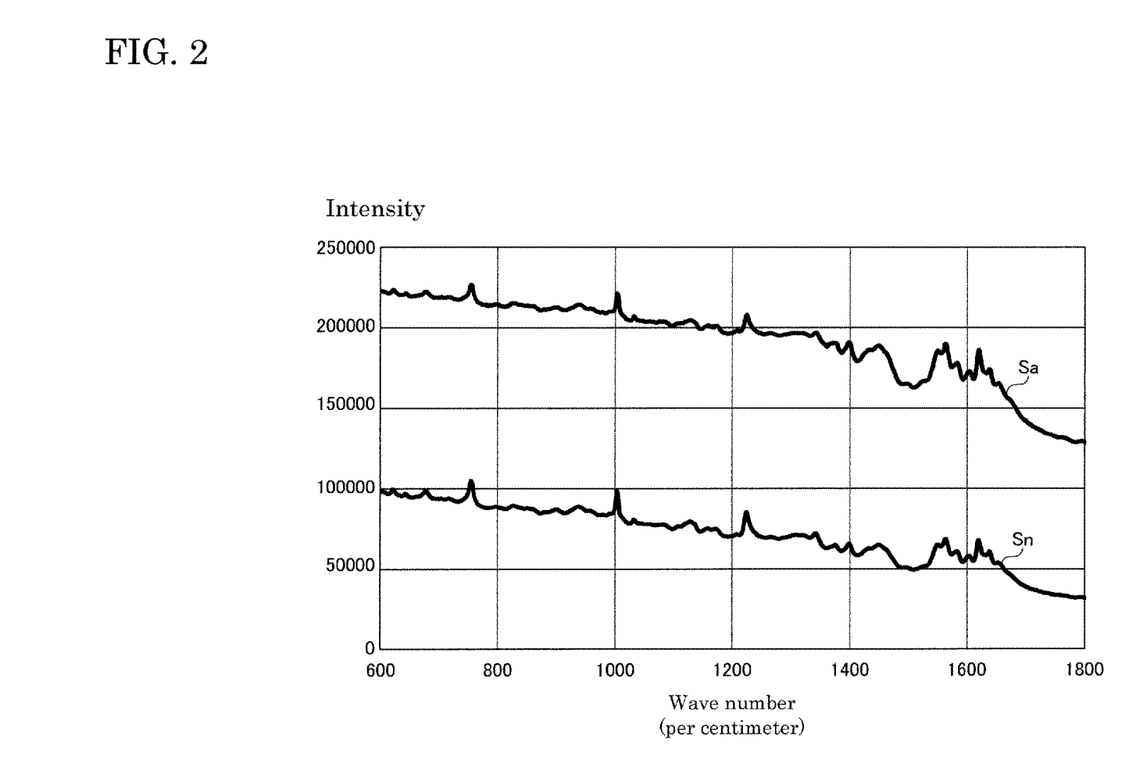
FIG. 2 is a diagram showing an example of spectra of blood.

FIG. 2 is a diagram showing an example of spectra of blood. Note that in FIG. 2, the abscissa indicates the Raman shift wavenumber, and the ordinate indicates the intensity. In Raman spectrum measurement, if the intensity of scattered light that has been detected is weak, excitation light may need to be irradiated for several tens of seconds to several minutes, for example.

As shown in FIG. 2, for example, a spectrum Sn is a spectrum of normal blood, and a spectrum Sa is a spectrum of blood including blood cells burned by excitation light.

For example, in the case of using Raman spectroscopy, if excitation light is focused on a blood vessel BV in the living body LB shown in FIG. 1, the blood cells contained in the blood vessel BV may be burned.

More specifically, the thinner the blood vessel BV is, the lower a blood flow rate vb of the blood in the blood vessel BV becomes. Specifically, the blood flow rates vb of arterioles, venules and capillary vessels are respectively about 5 mm/s, 2.5 mm/s and 1 mm/s, for example. Note that these blood flow rates vb may be lower depending on the physical condition or individual difference of a measurement target and the like.

In the case of measuring a Raman spectrum, the shorter the focal distance is, the easier the measurement becomes. Specifically, measurement of the Raman spectrum of blood flowing through a capillary vessel positioned at a depth Dv of 1 to 2 mm from a body surface Sf is easier than measurement of the Raman spectrum of blood flowing through arterioles, venules or the like at positions that are deeper than capillary vessels from the body surface Sf.

Moreover, a blood sugar value varies in accordance with a measurement site or a blood collecting position. For example, temporal change in the blood sugar value such as a rise in the postprandial blood sugar value varies depending on the position of the blood vessel BV of the living body LB. In the case of measuring the blood sugar value using Raman spectroscopy, calibration is performed using an actually measured value in order to convert the intensity of Raman scattered light into a blood sugar value. In the case of performing calibration using a blood sugar value measured by a conventional invasive blood sugar measurement device, for example, blood collected from a capillary vessel at a fingertip is often used as a measurement target, and the blood sugar value at the capillary vessel position of the fingertip is used as a reference. Therefore, the closer the position at which a blood sugar value is measured in a non-invasive manner using Raman spectroscopy is to the position at which the blood sugar value to be used for calibration is measured or a position at which blood is collected, the more accurate calibration can be performed. Therefore, also in the case of measuring the blood sugar value using Raman spectroscopy, measuring the blood sugar in a capillary vessel at the fingertip is desirable because it enables more accurate measurement.

In other words, although measurement of a Raman spectrum of blood in a capillary vessel is desired, the blood flow rate vb is low in the capillary vessel, and thus the same blood cells are irradiated with excitation light for a long time, increasing the possibility that the blood cells are burned.

Moreover, for example, it is conceivable to use CARS (Coherent anti-Stokes Raman spectroscopy) as in the monitor described in Patent Document 1, in order to measure a Raman spectrum with a favorable S/N ratio, but CARS requires strong excitation light, and thus has a higher possibility that blood cells are burned.

If strong excitation light is irradiated and blood cells are burned, the abnormal spectrum Sa that is different from the normal spectrum Sn is acquired as a measurement result. The abnormal spectrum Sa shows various characteristics, and as an example thereof, strong light occurs when the blood cells are burned, and thus as shown in FIG. 2, the signal intensity increases compared to the normal spectrum Sn. Therefore, for example, it becomes difficult to accurately measure the blood sugar in the blood.

In view of this, in the blood measuring apparatus according to the embodiments of the present invention, such an issue is solved by the following configurations and operations.

Returning to FIG. 1, the processing unit 7 holds the exposure duration Te, for example. Here, the exposure duration Te is set by the user, for example. The user sets the exposure duration Te in accordance with the blood flow rate vb or the like of the blood that is a measurement target. Specifically, for example, in the case where the blood flow rate vb of the blood vessel BV that is a measurement target is high, the user extends the exposure duration Te to the extent that the blood cells are not burned, and in the case where the blood flow rate vb in the blood vessel BV that is a measurement target is low, the user shortens the exposure duration Te to the extent that the blood cells are not burned.

For example, upon receiving movement completion information that will be described later from the control unit 3, the processing unit 7 outputs a measurement instruction including the exposure duration Te to the detector 4, and receives a spectrum from the detector 4 as a response to the measurement instruction.

For example, upon receiving the spectrum from the detector 4, the processing unit 7 outputs the received spectrum to the determination unit 5 and the calculation unit 6.

For example, the determination unit 5 performs, a plurality of times, determination processing for determining whether or not the irradiation position Ep is a blood vessel position of the living body LB, based on the spectrum detected by the detector 4.

Specifically, the determination unit 5 performs the determination processing based on the peak in the spectrum, for example.

More specifically, for example, upon receiving the spectrum from the processing unit 7, the determination unit 5 analyzes the received spectrum, and attempts detection of a peak originating from a blood component such as hemoglobin. For example, in the case where the determination unit 5 has detected a peak originating from a blood component, the determination unit 5 determines that the irradiation position Ep is a blood vessel position of the living body LB, and outputs blood vessel detection information indicating the determination result to the control unit 3 and the calculation unit 6.

On the other hand, for example, in the case where the determination unit 5 could not detect a peak originating from a blood component, the determination unit 5 determines that the irradiation position Ep is not a blood vessel position of the living body LB, and outputs blood vessel non-detection information indicating the determination result to the control unit 3 and the calculation unit 6.

Note that the determination unit 5 may perform the determination processing based on the band width of the peak that is based on Rayleigh scattering of excitation light in the spectrum. More specifically, for example, in the case where the determination unit 5 acquires the band width of the peak and detects a Doppler shift that is based on Rayleigh scattering of erythrocytes in the acquired band width, the determination unit 5 determines that the irradiation position Ep is a blood vessel position of the living body LB. On the other hand, for example, in the case where the determination unit 5 could not detect the Doppler shift in the acquired band width, the determination unit 5 determines that the irradiation position Ep is not a blood vessel position of the living body LB.

The control unit 3 adjusts the irradiation position Ep of the excitation light with which the living body LB is irradiated by the optical system 2. More specifically, the control unit 3 adjusts the irradiation position Ep such that the plurality of spectra are respectively detected at changed irradiation positions Ep.

For example, after determination processing is performed, the control unit 3 changes the irradiation position Ep, and performs the determination processing again. Specifically, the control unit 3 changes the irradiation position Ep every time the determination processing is performed. Accordingly, the control unit 3 limits the time during which the same irradiation position Ep is continuously irradiated with excitation light.

For example, the scanning mirror 34 can rotate using, as axes of rotation, two axes that pass through the center of the mirror, and are included in and are orthogonal to the mirror surface, in accordance with control by the control unit 3. For example, the excitation light irradiation position Ep in the living body LB is scanned in a direction (hereinafter, also referred to as a horizontal direction) that is orthogonal to the optical axis direction (hereinafter, also referred to as a vertical direction) of the objective lens 35, by the scanning mirror 34 rotating using each of the two axes as an axis of rotation, and thereby changing the reflection direction of the excitation light.

More specifically, upon receiving blood vessel detection information or blood vessel non-detection information from the determination unit 5, for example, the control unit 3 recognizes that the determination processing has been performed one time, and controls the scanning mirror 34 so as to move the irradiation position Ep in the horizontal direction.

At this time, for example, the control unit 3 may move the irradiation position Ep in the horizontal direction in accordance with a predetermined pattern, may randomly move the irradiation position Ep, or may reciprocate the irradiation position Ep between predetermined two points.

Note that the control unit 3 may move an optical element or the like in the blood measuring apparatus 101 other than the scanning mirror 34 as necessary, in order to move the irradiation position Ep in the horizontal direction.

Moreover, the present invention is not limited to a configuration in which the irradiation position Ep is changed by the scanning mirror 34 rotating, and a configuration may be adopted in which a plurality of optical systems 2 are arranged, and the irradiation position Ep is changed by switching the optical system 2 that is used for measurement. A configuration may also be adopted in which a plurality of scanning mirrors 34 and objective lenses 35 that are portions of the optical system 2 are arranged, and the irradiation position Ep is changed by switching the scanning mirror 34 and the objective lens 35 that are used for measurement.

For example, when the movement of the irradiation position Ep is completed, the control unit 3 outputs, to the processing unit 7, movement completion information indicating that the movement of the irradiation position Ep is completed.

Note that the present invention is not limited to a configuration in which when the movement of the irradiation position Ep is completed, the control unit 3 outputs the movement completion information to the processing unit 7, and the control unit 3 may be configured to, when the movement of the irradiation position Ep is completed, wait for a predetermined time or a random time and then outputs the movement completion information to the processing unit 7. The control unit 3 may also be configured to periodically output the movement completion information to the processing unit 7, by waiting as described above.

In the blood measuring apparatus 101, for example, a plurality of spectra detected by the detector 4 are integrated, and numerical value information regarding a substance included in the blood of the living body LB is measured based on the integration result.

More specifically, the calculation unit 6 integrates a plurality of spectra detected by the detector 4, for example. Specifically, for example, upon receiving blood vessel detection information from the determination unit 5, the calculation unit 6 saves, in the storage unit 8, the corresponding spectrum received from the processing unit 7. For example, when the number of spectra saved in the storage unit 8 reaches a predetermined number, the calculation unit 6 integrates the predetermined number of spectra saved in the storage unit 8, and outputs the integrated spectra obtained by integrating the spectra, to the analyzing unit 9.

In addition, for example, the calculation unit 6 excludes, as a target of integration, the spectrum corresponding to the irradiation position Ep determined in the determination processing not to be a blood vessel position. Specifically, for example, upon receiving blood vessel non-detection information from the determination unit 5, the calculation unit 6 discards the corresponding spectrum received from the processing unit 7.

Upon receiving the integrated spectra from the calculation unit 6, the analyzing unit 9 analyzes the received integrated spectra, for example. More specifically, for example, the analyzing unit 9 calculates the blood sugar concentration in the blood in the blood vessel BV from the integrated spectra, using a calibration curve, a conversion coefficient or the like, and displays, on a display unit (not illustrated), the calculated blood sugar concentration along with completion information indicating that measurement is completed.

In the blood measuring apparatus 101, a time Tp during which the same irradiation position Ep is continuously irradiated with excitation light is limited in this manner. The setting of this time Tp can be changed, for example. Here, for example, the time Tp is the total of the exposure duration Te and the time required for the determination processing.

The blood measuring apparatus is provided with a computer, and a calculation processing unit such as a CPU in the computer reads out, from a memory (not illustrated), a program including a portion of or all the steps of the flowchart that will be described below, and executes the program. This program of the apparatus can be installed from outside. This program of the apparatus is distributed in a state of being stored in a recording medium.

Figure 3:
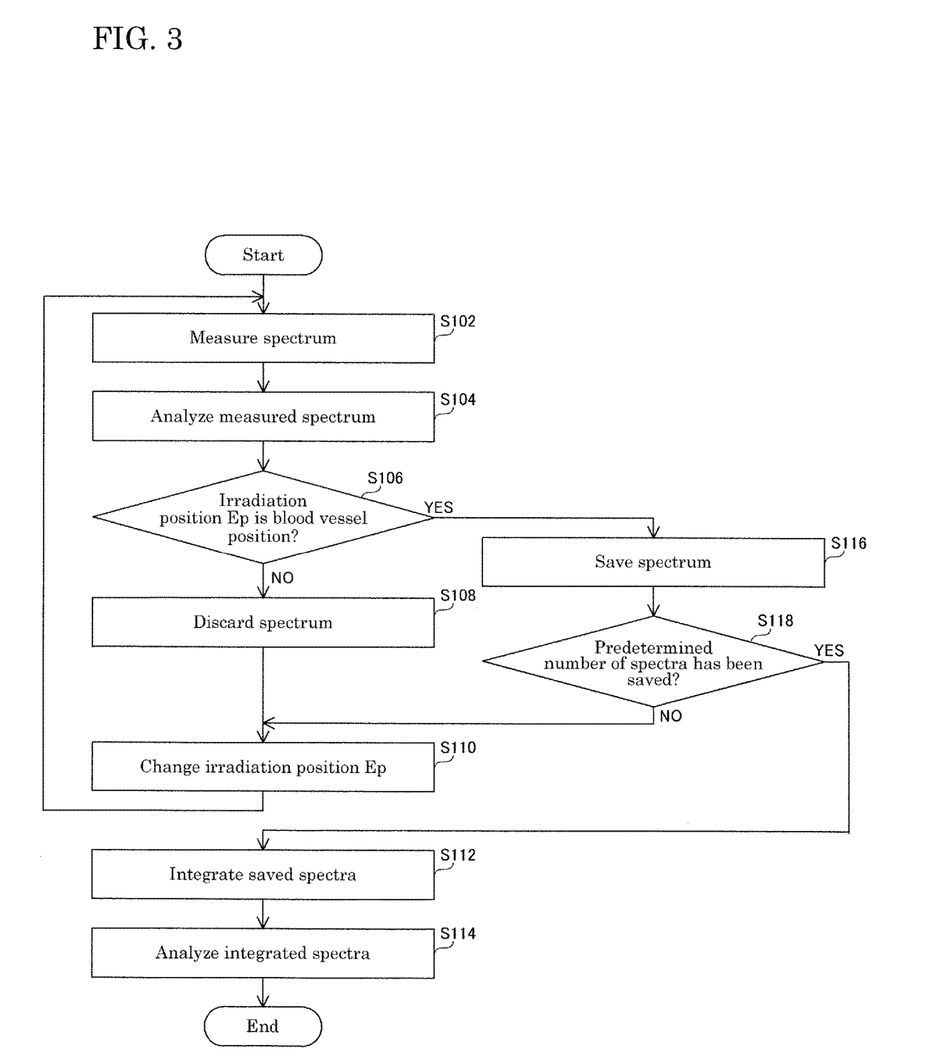
FIG. 3 is a flowchart that defines an operation procedure when the blood measuring apparatus according to the first embodiment of the present invention analyzes blood in a living body.

FIG. 3 is a flowchart that defines an operation procedure when the blood measuring apparatus according to the first embodiment of the present invention analyzes blood in a living body.

As shown in FIG. 3, for example, a situation is envisioned in which the light source 10 outputs excitation light with a constant power.

First, the blood measuring apparatus 101 measures the spectrum of scattered light that is based on the excitation light focused at the irradiation position Ep (step S102).

Next, the blood measuring apparatus 101 analyzes the measured spectrum (step S104), and determines, based on the analysis result, whether or not the irradiation position Ep is a blood vessel position (step S106).

If the blood measuring apparatus 101 determines that the irradiation position Ep is not a blood vessel position (step S106: NO), the blood measuring apparatus 101 discards the measured spectrum (step S108).

On the other hand, if the blood measuring apparatus 101 determines that the irradiation position Ep is a blood vessel position (step S106: YES), the blood measuring apparatus 101 saves the measured spectrum (step S116).

Next, the blood measuring apparatus 101 checks whether or not a predetermined number of spectra is saved (step S118).

In the case where the blood measuring apparatus 101 discards the measured spectrum (step S108), or where the blood measuring apparatus 101 confirms that the predetermined number of spectra is not saved (step S118: NO), the blood measuring apparatus 101 changes the irradiation position Ep (step S110).

Next, the blood measuring apparatus 101 newly measures the spectrum of the scattered light that is based on the excitation light focused at the changed irradiation position Ep (step S102).

On the other hand, in the case where the blood measuring apparatus 101 confirms that the predetermined number of spectra is saved (step S118: YES), the blood measuring apparatus 101 integrates the saved spectra (step S112).

Next, the blood measuring apparatus 101 analyzes the integrated spectra, and calculates the blood sugar concentration in the blood in the blood vessel BV, for example (step S114).

Note that description was given assuming that the blood measuring apparatus 101 is configured to discard the spectrum of a non-blood vessel position in the above step S108 every time the spectrum is measured, but the present invention is not limited thereto. For example, the blood measuring apparatus 101 may be configured to assign a mark to the spectrum of a non-blood vessel position and save the spectrum without discarding it in the above step S108, and to collectively discard spectra to which the mark is assigned, in the above step S112.

Description was also given assuming that the blood measuring apparatus according to the first embodiment of the present invention is configured to integrate a plurality of spectra detected by the detector 4, and to measure numerical value information regarding a substance included in the blood of the living body LB based on the integration result, but the present invention is not limited thereto. A configuration may be adopted in which processing for integrating a plurality of spectra detected by the detector 4 and processing for measuring numerical value information regarding a substance included in the blood of the living body LB based on the integration result are performed by a terminal apparatus such as a computer provided outside of the blood measuring apparatus 101. In other words, the calculation unit 6, the storage unit 8 and the analyzing unit 9 in the blood measuring apparatus 101 may be provided outside of the blood measuring apparatus 101.

Incidentally, there is a desire for a technique that enables excellent blood measurement beyond the techniques described in Non-patent Document 1 and Patent Document 1.

For this reason, in the blood measuring apparatus according to the first embodiment of the present invention, the optical system 2 irradiates the living body LB with excitation light from the light source 10, and guides Raman scattered light from the living body LB to the spectroscope 1. The control unit 3 adjusts the irradiation position Ep at which the living body LB is irradiated with the excitation light by the optical system 2. The detector 4 detects the spectrum of the Raman scattered light using light of each wavelength dispersed by the spectroscope 1. A plurality of spectra detected by the detector 4 are integrated, and numerical value information regarding a substance included in the blood of the living body LB is measured based on the integration result. The control unit 3 then adjusts the irradiation position Ep such that the plurality of spectra are detected at changed irradiation positions Ep.

With such a configuration, it is possible to avoid a situation in which the same position is continuously irradiated with excitation light, and thus even in the case where blood is present at the irradiation position Ep, for example, damage to the blood can be reduced. This makes it possible to measure an excellent spectrum of blood that is not damaged. Therefore, the blood can be favorably measured.

In addition, in the blood measuring apparatus according to the first embodiment of the present invention, the determination unit 5 performs determination processing for determining, based on a spectrum detected by the detector 4, whether or not the irradiation position Ep is a blood vessel position of the living body LB. The determination unit 5 performs the determination processing a plurality of times. The control unit 3 then changes the irradiation position Ep, after the determination processing is performed.

With such a configuration, the irradiation position Ep can be changed at an appropriate timing that is based on the determination processing, while performing the determination processing that is useful for checking the quality of the measured spectrum, and thus damage to the blood can be more reliably reduced.

In addition, in the blood measuring apparatus according to the first embodiment of the present invention, the calculation unit 6 integrates a plurality of spectra detected by the detector 4. The calculation unit 6 then excludes, as a target of integration, a spectrum corresponding to the irradiation position Ep determined in the determination processing not to be a blood vessel position.

With a configuration in which a spectrum that is based on Raman scattered light from the irradiation position Ep determined not to be a blood vessel position is excluded as a target of integration in this manner, the spectra of normal blood can be selected and integrated, and thus a more excellent spectrum can be obtained.

In addition, in the blood measuring apparatus according to the first embodiment of the present invention, the time Tp during which the same irradiation position Ep is continuously irradiated with excitation light is limited. Also, the setting of the time Tp can be changed.

With such a configuration, for example, the time Tp can be set in accordance with the blood flow rate vb in the blood vessel BV, which is a measurement target, and thus it is possible to provide a user-friendly apparatus that can measure a more favorable spectrum of blood while more reliably reducing damage to the blood.

Note that description was given assuming that the blood measuring apparatus according to the first embodiment of the present invention is configured to change the irradiation position Ep every time the determination processing is performed, but the present invention is not limited thereto.

The blood measuring apparatus 101 may be configured to determine whether or not an irradiation time of excitation light to the same position has exceeded the time Tp, and to change the irradiation position Ep in the case where the irradiation time has exceeded the time Th.

Next, another embodiment of the present invention will be described with reference to the drawings. Note that in the drawings, the same reference signs are given to the same or equivalent constituent elements, and description thereof is not repeated.

Second Embodiment

This embodiment relates to a blood measuring apparatus that changes the irradiation range of excitation light, or changes the irradiation intensity of excitation light, in comparison to the blood measuring apparatus according to the first embodiment. Except for the contents to be described below, the blood measuring apparatus according to this embodiment is similar to the blood measuring apparatus according to the first embodiment.

Figure 4:
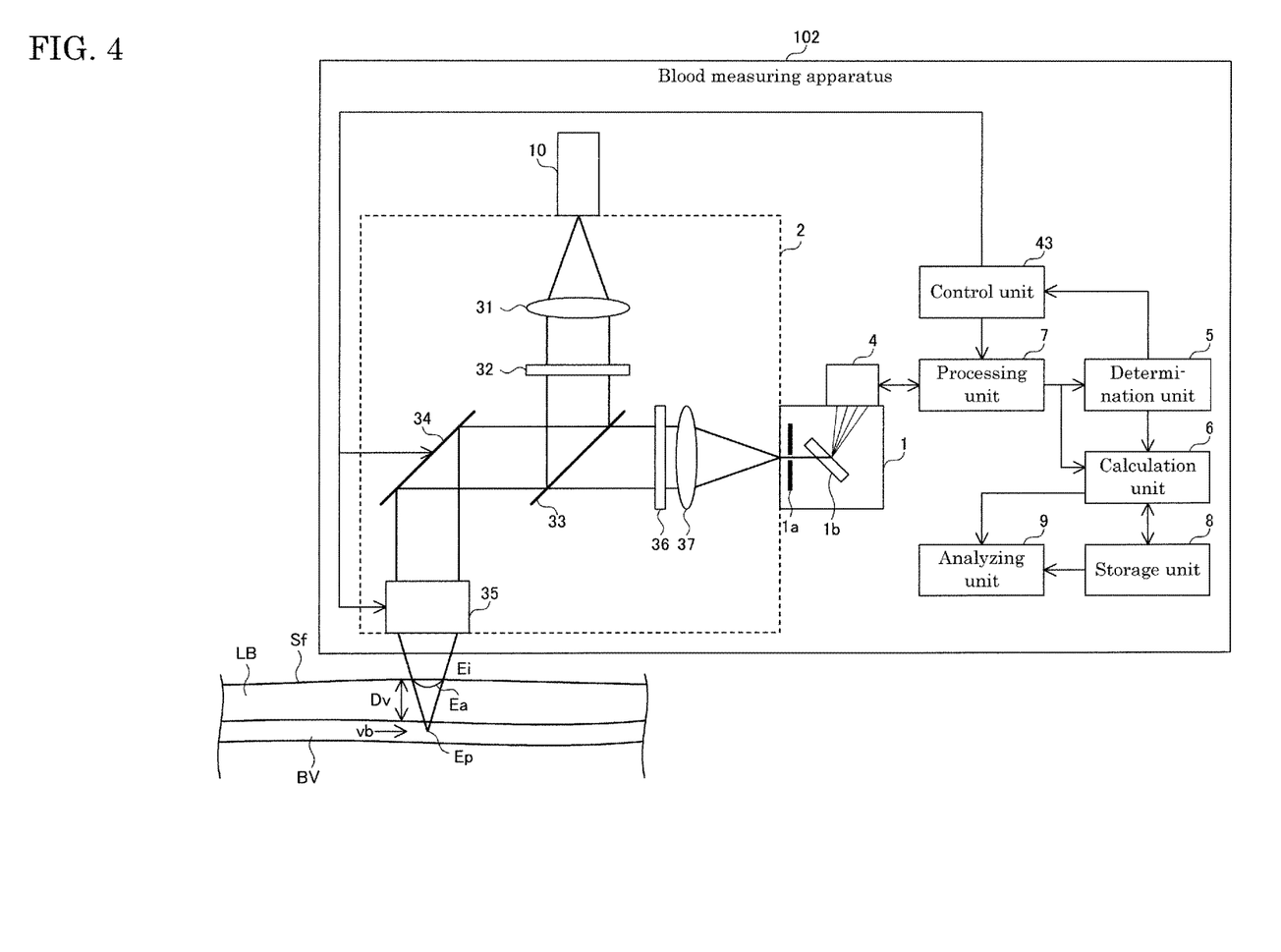
FIG. 4 is a diagram showing a configuration of a blood measuring apparatus according to a second embodiment of the present invention.

FIG. 4 is a diagram showing the configuration of the blood measuring apparatus according to the second embodiment of the present invention.

As shown in FIG. 4, a blood measuring apparatus 102 is provided with a spectroscope 1, an optical system 2, a control unit 43, a detector 4, a determination unit 5, a calculation unit 6, a processing unit 7, a storage unit 8, an analyzing unit 9 and a light source 10.

The configurations and operations of the spectroscope 1, the optical system 2, the detector 4, the determination unit 5, the calculation unit 6, the processing unit 7, the storage unit 8, the analyzing unit 9 and the light source 10 in the blood measuring apparatus 102 are respectively similar to those of the spectroscope 1, the optical system 2, the detector 4, the determination unit 5, the calculation unit 6, the processing unit 7, the storage unit 8, the analyzing unit 9 and the light source 10 in the blood measuring apparatus 101 shown in FIG. 1.

The optical system 2 irradiates the living body LB with light from the light source 10, and guides Raman scattered light from the living body LB to the spectroscope 1.

The detector 4 detects the spectrum of the Raman scattered light dispersed by the spectroscope 1. Specifically, for example, upon receiving a measurement instruction from the processing unit 7, the detector 4 measures the spectrum by accumulating, for the exposure duration Te, the intensity of the scattered light for each wavelength diffracted by the diffraction lattice 1b, and outputs the measured spectrum to the processing unit 7.

For example, upon receiving change completion information Ia that will be described later, or movement completion information from the control unit 43, the processing unit 7 outputs a measurement instruction that includes the exposure duration Te to the detector 4, and receives a spectrum from the detector 4 as a response to the measurement instruction.

For example, upon receiving the spectrum from the detector 4, the processing unit 7 outputs the received spectrum to the determination unit 5 and the calculation unit 6.

For example, the determination unit 5 performs determination processing for determining, based on the spectrum detected by the detector 4, whether or not the irradiation position Ep is a blood vessel position of the living body LB.

For example, in the case where the determination unit 5 has detected a peak originating from a blood component, the determination unit 5 determines in the determination processing that the irradiation position Ep is a blood vessel position of the living body LB, and outputs blood vessel detection information indicating the determination result to the control unit 43 and the calculation unit 6.

For example, on the other hand, in the case where the determination unit 5 could not detect a peak originating from a blood component, the determination unit 5 determines in the determination processing that the irradiation position Ep is not a blood vessel position of the living body LB, and outputs blood vessel non-detection information indicating the determination result to the control unit 43 and the calculation unit 6.

For example, in the case where it was determined in the determination processing that the irradiation position Ep is not a blood vessel position, the control unit 43 changes the irradiation position Ep.

For example, the objective lens 35 can move along the optical axis of excitation light, in accordance with control by the control unit 43. For example, the focus of excitation light, namely, the irradiation position Ep moves in the vertical direction, by the objective lens 35 moving in this manner.

The control unit 43 performs search processing for searching for a blood vessel position at the time of starting measurement by the blood measuring apparatus 102 to which the control unit 43 belongs, for example.

More specifically, for example, the control unit 43 controls at least one of the scanning mirror 34 and the objective lens 35 so as to move the irradiation position Ep in at least one of the horizontal direction and the vertical direction. For example, when the movement of the irradiation position Ep is completed, the control unit 43 outputs movement completion information to the processing unit 7.

For example, upon receiving, from the determination unit 5, blood vessel non-detection information as a result of the determination processing that is based on the spectrum after the movement of the irradiation position Ep, the control unit 43 further moves the irradiation position Ep in at least one of the horizontal direction and the vertical direction, and outputs movement completion information to the processing unit 7.

On the other hand, for example, upon receiving, from the determination unit 5, blood vessel detection information as a result of the determination processing that is based on the spectrum after the movement of the irradiation position Ep, the control unit 43 ends the search processing.

The control unit 43 adjusts an irradiation range Ea of excitation light with which the living body LB is irradiated by the optical system 2. Here, as shown in FIG. 4, for example, the irradiation range Ea is a range Ea in which the body surface Sf of the living body LB is irradiated with excitation light. Also, as shown in FIG. 4, an irradiation intensity Ei is power per unit area in the irradiation range Ea on the body surface Sf of the living body LB, for example.

More specifically, after a spectrum is detected by the detector 4, the control unit 43 performs adjustment processing AP2 for enlarging the irradiation range Ea and then restoring the irradiation range Ea. For example, the control unit 43 performs the adjustment processing AP2, in the case where it was determined in the determination processing that the irradiation position Ep is a blood vessel position.

Specifically, the control unit 43 stores the position of the objective lens 35 at the time of the end of the search processing. At the timing of receiving the blood vessel detection information from the determination unit 5, the control unit 43 then enlarges the irradiation range Ea by moving the objective lens 35 in a direction approaching the living body LB, for example.

With such a configuration, the focus of excitation light moves in a direction away from the body surface Sf, and thus it is possible to reduce the energy of excitation light that is received by the same blood cells of the blood in the blood vessel BV. This makes it possible to suppress damage to the blood.

Note that the control unit 43 may reduce, at the above timing, the irradiation range Ea by moving the objective lens 35 in a direction away from the living body LB, for example.

With such a configuration, the focus of excitation light moves in a direction approaching the body surface Sf, and thus it is possible to reduce the energy of excitation light that is received by the same blood cells of the blood in the blood vessel BV. This makes it possible to suppress damage to the blood.

For example, after moving the objective lens 35, the control unit 43 waits for a waiting time Tw. For example, when the waiting time Tw has elapsed, the control unit 43 restores the irradiation range Ea by moving the objective lens 35 to a stored position, and outputs, to the processing unit 7, the change completion information Ia indicating that the irradiation range Ea was changed and then restored.

For example, upon receiving the change completion information Ia from the control unit 43, the processing unit 7 outputs a measurement instruction that includes the exposure duration Te to the detector 4.

After the adjustment processing AP2 was performed, the detector 4 detects a new spectrum. Specifically, for example, upon receiving the measurement instruction from the processing unit 7, the detector 4 measures a new spectrum by accumulating the intensity of scattered light for each wavelength diffracted by the diffraction lattice 1*b* for the exposure duration Te. The detector 4 then outputs the measured new spectrum to the processing unit 7, for example.

In the blood measuring apparatus 102, excitation light having the irradiation range Ea of a predetermined size and the irradiation intensity Ei of a predetermined magnitude is irradiated to the living body LB in order to detect a spectrum, and a duration Ta for the irradiation range Ea of the predetermined size is limited, in this manner. The setting of this duration Ta can be changed, for example. Here, the duration Ta is the total of the exposure duration Te and the time required for the determination processing, for example.

Note that description was given assuming that the blood measuring apparatus according to the second embodiment of the present invention has a configuration in which, after a spectrum is detected by the detector 4, the control unit 43 moves the objective lens 35 so as to enlarge the irradiation range Ea, and then restores the irradiation range Ea by moving the objective lens 35 to a stored position, but the present invention is not limited thereto. It is sufficient that the control unit 43 is configured to enlarge the irradiation range Ea and then reduce the irradiation range Ea. Also in the case where the control unit 43 enlarges the irradiation range Ea and then restores the irradiation range Ea, the restored irradiation range Ea may be slightly different from the original irradiation range Ea.

Figure 5:
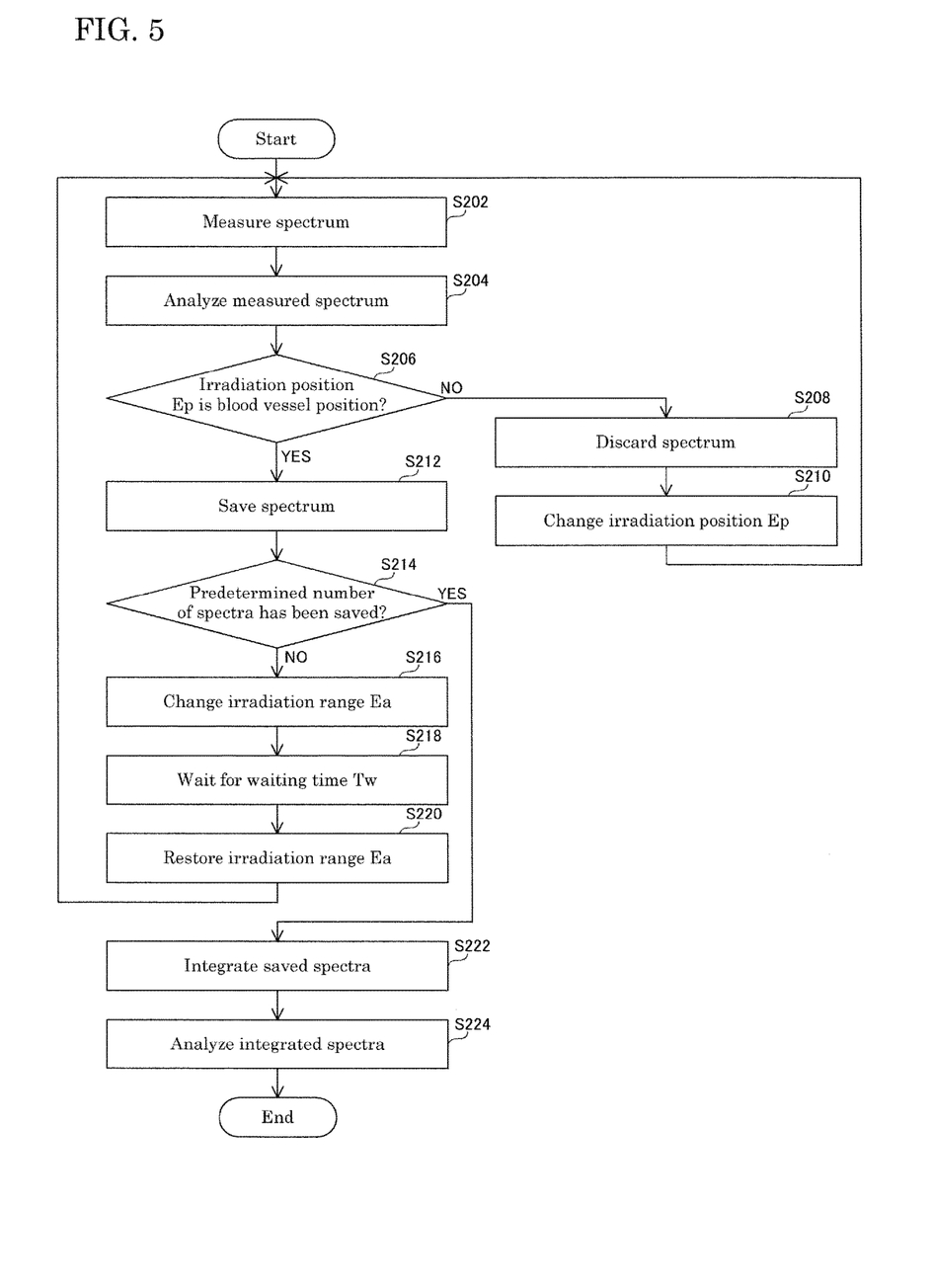
FIG. 5 is a flowchart that illustrates an operation procedure when the blood measuring apparatus according to the second embodiment of the present invention analyzes blood in a living body.

FIG. 5 is a flowchart that defines an operation procedure when the blood measuring apparatus according to the second embodiment of the present invention analyzes blood in a living body.

As shown in FIG. 5, first, the blood measuring apparatus 102 measures the spectrum of scattered light that is based on excitation light focused at the irradiation position Ep (step S202).

Next, the blood measuring apparatus 102 analyzes the measured spectrum (step S204), and determines, based on the analysis result, whether or not the irradiation position Ep is a blood vessel position (step S206).

If the blood measuring apparatus 102 determines that the irradiation position Ep is not a blood vessel position (step S206: NO), the blood measuring apparatus 102 discards the measured spectrum (step S208).

Next, the blood measuring apparatus 102 changes the irradiation position Ep (step S210).

Next, the blood measuring apparatus 102 newly measures the spectrum of scattered light that is based on excitation light focused at the changed irradiation position Ep (step S202).

On the other hand, if the blood measuring apparatus 102 determines that the irradiation position Ep is a blood vessel position (step S206: YES), the blood measuring apparatus 102 saves the measured spectrum (step S212).

Next, if the blood measuring apparatus 102 confirms that a predetermined number of spectra is not saved (step S214: NO), the blood measuring apparatus 102 changes the irradiation range Ea (step S216).

Next, the blood measuring apparatus 102 waits for the waiting time Tw (step S218).

Next, the blood measuring apparatus 102 restores the irradiation range Ea (step S220).

Next, the blood measuring apparatus 102 newly measures the spectrum of scattered light that is based on excitation light focused at the irradiation position Ep (step S202).

On the other hand, in the case where the blood measuring apparatus 102 confirms that a predetermined number of spectra is saved (step S214: YES), the blood measuring apparatus 102 integrates the saved spectra (step S222).

Next, the blood measuring apparatus 102 analyzes the integrated spectra, and for example, calculates the blood sugar concentration in the blood in the blood vessel BV (step S224).

Figure 6:
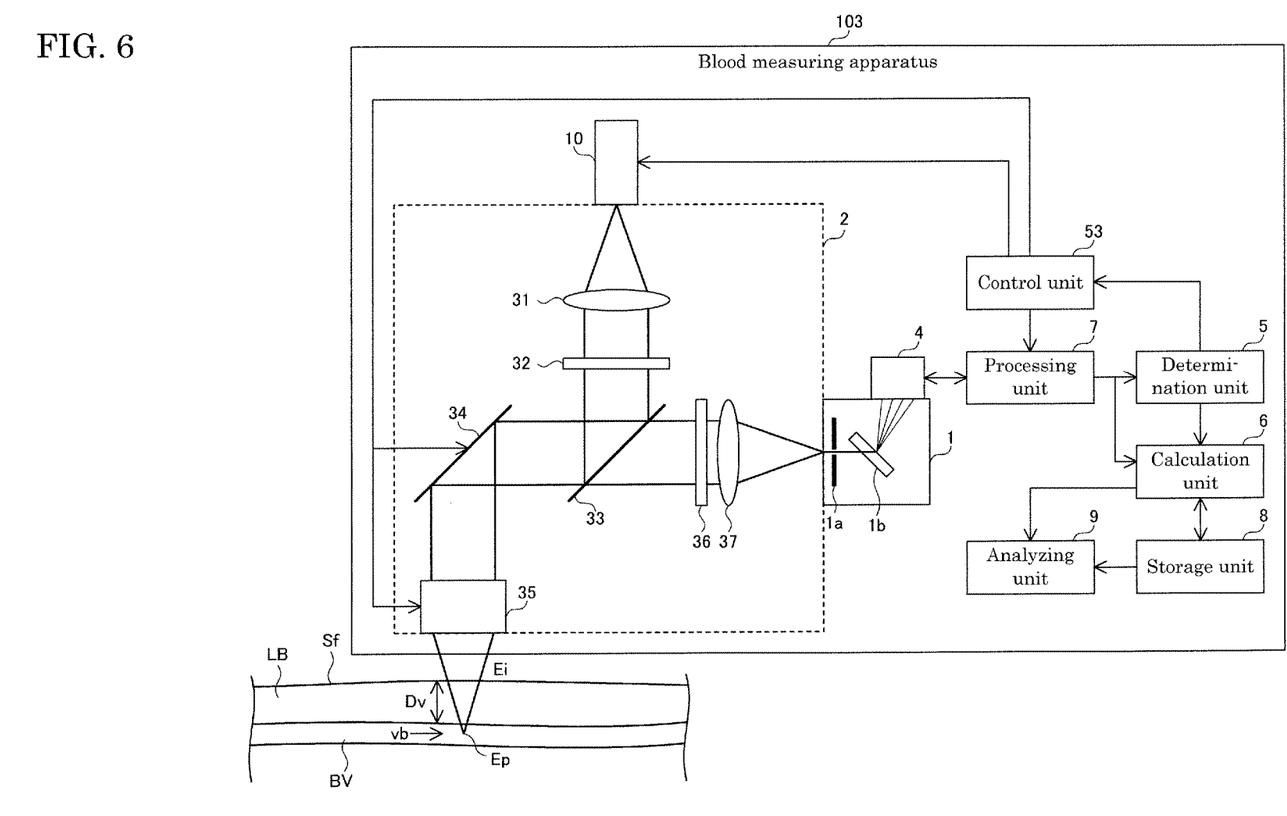
FIG. 6 is a diagram showing a configuration of a modified example of the blood measuring apparatus according to the second embodiment of the present invention.

FIG. 6 is a diagram showing the configuration of a modified example of the blood measuring apparatus according to the second embodiment of the present invention.

As shown in FIG. 6, a blood measuring apparatus 103, which is a modified example of the blood measuring apparatus 102, is provided with a control unit 53 in place of the control unit 43, in comparison with the blood measuring apparatus 102 shown in FIG. 4.

The configurations and operations of a spectroscope 1, an optical system 2, a detector 4, a determination unit 5, a calculation unit 6, a processing unit 7, a storage unit 8, an analyzing unit 9 and a light source 10 in the blood measuring apparatus 103 are respectively similar to those of the spectroscope 1, the optical system 2, the detector 4, the determination unit 5, the calculation unit 6, the processing unit 7, the storage unit 8, the analyzing unit 9 and the light source 10 in the blood measuring apparatus 102 shown in FIG. 4.

The optical system 2 irradiates the living body LB with light from the light source 10, and guides Raman scattered light from the living body LB to the spectroscope 1. For example, upon receiving a measurement instruction from the processing unit 7, the detector 4 measures a spectrum by accumulating, for the exposure duration Te, the intensity of scattered light for each wavelength diffracted by the diffraction lattice 1*b* and outputs the measured spectrum to the processing unit 7.

For example, upon receiving change completion information Ii that will be described later or movement completion information from the control unit 53, the processing unit 7 outputs, to the detector 4, a measurement instruction that includes the exposure duration Te, and receives, from the detector 4, a spectrum as a response to the measurement instruction.

For example, upon receiving the spectrum from the detector 4, the processing unit 7 outputs the received spectrum to the determination unit 5 and the calculation unit 6.

For example, the determination unit 5 performs determination processing for determining, based on the spectrum detected by the detector 4, whether or not the irradiation position Ep is a blood vessel position of the living body LB.

In the case where it was determined in the determination processing that the irradiation position Ep is not a blood vessel position, the control unit 53 changes the irradiation position Ep, for example.

The control unit 53 performs search processing for searching for a blood vessel position, at the time of starting measurement by the blood measuring apparatus 103 to which the control unit 53 belongs, for example.

More specifically, for example, the control unit 53 controls at least one of the scanning mirror 34 and the objective lens 35 so as to move the irradiation position Ep in at least one of the horizontal direction or the vertical direction. For example, when the movement of the irradiation position Ep is completed, the control unit 53 outputs movement completion information to the processing unit 7.

For example, upon receiving, from the determination unit 5, blood vessel non-detection information as a result of determination processing that is based on a spectrum after the movement of the irradiation position Ep, the control unit 53 further moves the irradiation position Ep in at least one of the horizontal direction and the vertical direction, and outputs movement completion information to the processing unit 7.

On the other hand, for example, upon receiving, from the determination unit 5, blood vessel detection information as a result of determination processing that is based on a spectrum after the movement of the irradiation position Ep, the control unit 53 ends the search processing.

The control unit 53 adjusts the irradiation intensity Ei of excitation light with which the living body LB is irradiated by the optical system 2. More specifically, after a spectrum is detected by the detector 4, the control unit 53 performs adjustment processing AP3 for reducing the irradiation intensity Ei and then restoring the original irradiation intensity Ei. For example, in the case where it was determined in determination processing that the irradiation position Ep is a blood vessel position, the control unit 53 performs the adjustment processing AP3.

Specifically, for example, the light source 10 can change the power of laser light to be output, in accordance with control by the control unit 53.

Moreover, for example, the control unit 53 stores the power value of output light of the light source 10 at the time of the end of search processing. The control unit 53 then performs control so as to reduce the power of the output light of the light source 10, at the timing of receiving blood vessel detection information from the determination unit 5.

With such a configuration, the irradiation intensity Ei of excitation light decreases, and thus it is possible to reduce the energy of excitation light received by the same blood cells of the blood in the blood vessel BV. This makes it possible to suppress damage to the blood.

After performing the control so as to reduce the power of the output light of the light source 10, the control unit 53 wait for the waiting time Tw, for example. When the waiting time Tw has elapsed, for example, the control unit 53 restores the original irradiation intensity Ei of excitation light by performing control so as to restore the power of the output light of the light source 10 to the stored power value, and outputs, to the processing unit 7, the change completion information Ii indicating that the irradiation intensity Ei has been changed and then restored.

For example, upon receiving the change completion information Ii from the control unit 53, the processing unit 7 outputs a measurement instruction including the exposure duration Te to the detector 4.

In the blood measuring apparatus 103, the living body LB is irradiated with excitation light having the irradiation range Ea of a predetermined size and the irradiation intensity Ei of a predetermined magnitude in this manner in order to detect a spectrum, and a duration Ti for the irradiation intensity Ei of the predetermined magnitude is limited. The setting of this duration Ti can be changed, for example. Here, the duration Ti is the total of the exposure duration Te and the time required for the determination processing, for example.

Figure 7:
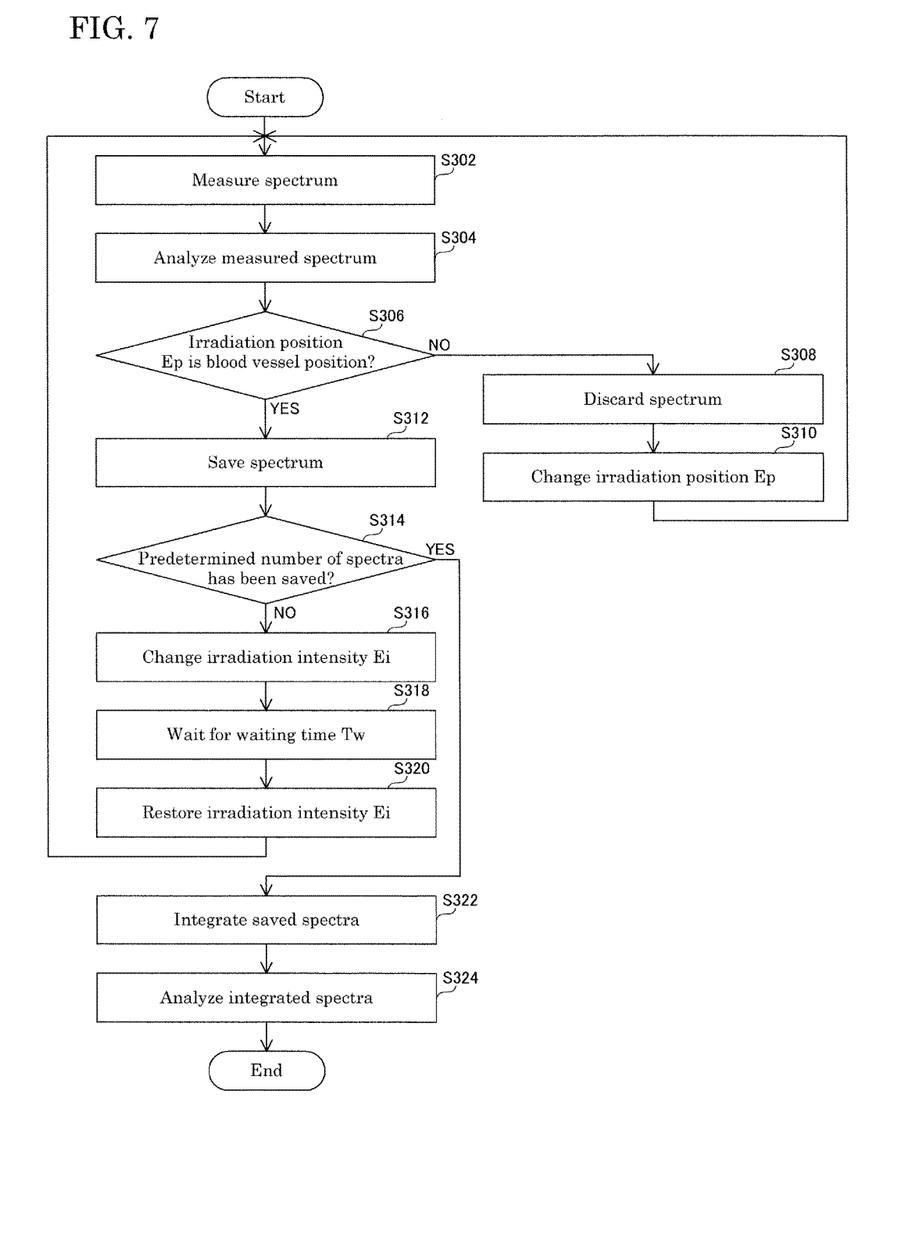
FIG. 7 is a flowchart that illustrates an operation procedure when the modified example of the blood measuring apparatus according to the second embodiment of the present invention analyzes blood in a living body.

FIG. 7 is a flowchart that defines an operation procedure when the modified example of the blood measuring apparatus according to the second embodiment of the present invention analyzes blood in a living body.

As shown in FIG. 7, the operations of steps S302 to S314 are respectively similar to the operations of steps S202 to S214 shown in FIG. 5.

Next, in the case where the blood measuring apparatus 103 confirmed that a predetermined number of spectra is not saved (step S314: NO), the blood measuring apparatus 103 changes the irradiation intensity Ei (step S316).

Next, the blood measuring apparatus 103 waits for the waiting time Tw (step S318).

Next, the blood measuring apparatus 103 restores the original irradiation intensity Ei (step S320).

The operations of steps S322 to S324 are respectively similar to the operations of steps S222 to S224 shown in FIG. 5.

Note that description was given assuming that the blood measuring apparatus according to the second embodiment of the present invention has a configuration in which the duration Ta for the irradiation range Ea of a predetermined size or the duration Ti for the irradiation intensity Ei of a predetermined magnitude is limited, but the present invention is not limited thereto. The blood measuring apparatus may have a configuration in which both the duration Ta and the duration Ti are limited.

Description was also given assuming that the blood measuring apparatus according to the second embodiment of the present invention is configured to integrate a plurality of spectra detected by the detector 4, and to measure numerical value information regarding a substance included in the blood of the living body LB based on the integration result, but the present invention is not limited thereto. A configuration may be adopted in which processing for integrating a plurality of spectra detected by the detector 4 and processing for measuring numerical value information regarding a substance included in the blood of the living body LB based on the integration result are performed by a terminal apparatus such as a computer provided outside of the blood measuring apparatus 102 or 103. In other words, the calculation unit 6, the storage unit 8 and the analyzing unit 9 in the blood measuring apparatus 102 or 103 may be respectively provided outside of the blood measuring apparatus 102 or 103.

Description was also given assuming that the blood measuring apparatus according to the second embodiment of the present invention has a configuration in which the control unit 53 performs control so as to reduce the power of output light of the light source 10, and then performs control so as to return the power of the output light of the light source 10 to a stored power value so as to restore the irradiation intensity Ei of excitation light, but the present invention is not limited thereto. It is sufficient that the control unit 53 is configured to reduce the irradiation intensity Ei, and to then enlarge the irradiation intensity Ei. Also, in the case where the control unit 53 reduces the irradiation intensity Ei and then restores the irradiation intensity Ei, the restored irradiation intensity Ei may be slightly different from the original irradiation intensity Ei.

As described above, in the blood measuring apparatus according to the second embodiment of the present invention, the optical system 2 irradiates the living body LB with excitation light from the light source 10, and guides Raman scattered light from the living body LB to the spectroscope 1. The control unit 43 adjusts the irradiation range Ea with which the living body LB is irradiated with the excitation light by the optical system 2. The detector 4 detects the spectrum of the Raman scattered light dispersed by the spectroscope 1. A plurality of spectra detected by the detector 4 are integrated, and numerical value information regarding a substance included in the blood of the living body LB is measured based on the integration result. After a spectrum is detected by the detector 4, the control unit 43 performs the adjustment processing AP2 for enlarging the irradiation range Ea and then restoring the irradiation range Ea. After the adjustment processing AP2 is performed, the detector 4 detects a new spectrum.

With such a configuration, it is possible to avoid a situation in which excitation light is continuously focused at the same position, and thus in the case where blood is present at the irradiation position Ep of the excitation light with which the living body LB is irradiated, for example, damage to the blood can be reduced. This makes it possible to measure an excellent spectrum of the blood that is not damaged. Therefore, the blood can be favorably measured.

Also, in the blood measuring apparatus according to the second embodiment of the present invention, the optical system 2 irradiates the living body LB with excitation light from the light source 10, and guides Raman scattered light from the living body LB to the spectroscope 1. The control unit 53 adjusts the irradiation intensity Ei with which the living body LB is irradiated with the excitation light by the optical system 2. The detector 4 detects the spectrum of the Raman scattered light dispersed by the spectroscope 1. A plurality of spectra detected by the detector 4 are integrated, and numerical value information regarding a substance included in the blood of the living body LB is measured based on the integration result. After a spectrum is detected by the detector 4, the control unit 53 performs the adjustment processing AP3 for reducing the irradiation intensity Ei and then restoring the irradiation intensity Ei. After the adjustment processing AP3 is performed, the detector 4 detects a new spectrum.

With such a configuration, it is possible to avoid a situation in which the same position is continuously irradiated with excitation light at a strong intensity, and thus even in the case where blood is present at the irradiation position Ep at which the living body LB is irradiated with the excitation light, for example, damage to the blood can be reduced. This makes it possible to measure an excellent spectrum of the blood that is not damaged. Therefore, the blood can be favorably measured.

Moreover, in the blood measuring apparatus according to the second embodiment of the present invention, the determination unit 5 determines, based on a spectrum detected by the detector 4, whether or not the irradiation position Ep at which the living body LB is irradiated with excitation light is a blood vessel position of the living body LB. Subsequently, the control unit 43, in the case where it is determined in the determination processing that the irradiation position Ep is a blood vessel position, performs the adjustment processing AP2, and in the case where it is determined in the determination processing that the irradiation position Ep is not a blood vessel position, changes the irradiation position Ep.

With such a configuration, for example, at the time of starting measurement, a blood vessel position can be reliably searched for, and it is also possible to more reliably reduce damage to the blood while performing determination processing that is useful for checking the quality of the measured spectrum.

Moreover, in the blood measuring apparatus according to the second embodiment of the present invention, the determination unit 5 determines, based on a spectrum detected by the detector 4, whether or not the irradiation position Ep at which the living body LB is irradiated with excitation light is a blood vessel position of the living body LB. Subsequently, the control unit 53, in the case where it was determined in the determination processing that the irradiation position Ep is not a blood vessel position, changes the irradiation position Ep, and in the case where it was determined in the determination processing that the irradiation position Ep is a blood vessel position, performs the adjustment processing AP3.

With such a configuration, it is possible to more reliably reduce damage to the blood, while more reliably searching for a blood vessel position at the time of starting measurement, for example.

Moreover, in the blood measuring apparatus according to the second embodiment of the present invention, the calculation unit 6 integrates a plurality of spectra detected by the detector 4. The calculation unit 6 then excludes, as a target of integration, a spectrum corresponding to the irradiation position Ep determined in the determination processing not to be a blood vessel position.

With a configuration in which a spectrum that is based on Raman scattered light from the irradiation position Ep determined not to be a blood vessel position is excluded as a target of integration in this manner, it is possible to select and integrate the spectra of normal blood, and thus a more excellent spectrum can be obtained.

Moreover, in the blood measuring apparatus according to the second embodiment of the present invention, the living body LB is irradiated with excitation light having the irradiation range Ea of a predetermined size and the irradiation intensity Ei of a predetermined magnitude in order to detect a spectrum, and at least one of the duration Ta for the irradiation range Ea of a predetermined size and the duration Ti for the irradiation intensity Ei of a predetermined magnitude is limited. Also, the setting of the limited duration Ta or Ti can be changed.

With such a configuration, for example, the duration Ta or Ti can be set in accordance with the blood flow rate vb in the blood vessel BV that serves as a measurement target, and thus it is possible to provide a user-friendly apparatus that can measure a more excellent spectrum of blood while more reliably reducing damage to the blood.

Other configurations and operations are similar to those of the blood measuring apparatus according to the first embodiment, and thus detailed description is not repeated here.

Note that a portion of or all the constituent elements and operations of each of the apparatuses according to the first and second embodiments of the present invention can be combined as appropriate.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A blood measuring apparatus comprising:
    a spectroscope;
    an optical system configured to irradiate a blood vessel in a living body with excitation light from a light source, and to guide, to the spectroscope, Raman scattered light from the living body;
    a control unit configured to adjust an irradiation position at which the living body is irradiated with the excitation light by the optical system;
    a detector configured to detect a spectrum of the Raman scattered light using light of each wavelength dispersed by the spectroscope; and
    a determination unit configured to perform determination processing for determining, based on the spectrum detected by the detector, whether or not an irradiation position of the excitation light with which the living body is irradiated is a blood vessel position of the living body,
    wherein a plurality of spectra of scattered light from the blood vessel detected by the detector are integrated, and numerical value information regarding a substance included in blood of the living body is measured based on an integration result; and
    the control unit adjusts the irradiation position such that the plurality of spectra are detected at changed positions based on a determination result by the determination unit and measures the numerical value information regarding the substance included in the blood of the living body based on the integration result of the plurality of spectra detected at the changed positions.

2. The blood measuring apparatus according to claim 1, wherein the determination unit performs the determination processing a plurality of times, and
    the control unit changes the irradiation position after the determination processing is performed.

3. The blood measuring apparatus according to claim 2, further comprising:
    a calculation unit configured to integrate the plurality of spectra detected by the detector,
    wherein the calculation unit excludes, as an integration target, the spectrum corresponding to the irradiation position determined in the determination processing not to be the blood vessel position.

4. The blood measuring apparatus according to claim 1, wherein
    a time during which the same irradiation position is continuously irradiated with the excitation light is limited, and
    a setting of the time can be changed.

5. A blood measuring apparatus comprising:
    a spectroscope;
    an optical system configured to irradiate a blood vessel in a living body with excitation light from a light source, and to guide, to the spectroscope, Raman scattered light from the living body;
    a control unit configured to adjust an irradiation range or an irradiation intensity of the excitation light with which the living body is irradiated by the optical system; and
    a detector configured to detect a spectrum of the Raman scattered light dispersed by the spectroscope; and
    a determination unit configured to perform determination processing for determining, based on the spectrum detected by the detector, whether or not an irradiation position of the excitation light with which the living body is irradiated is a blood vessel position of the living body,
    wherein a plurality of spectra of scattered light from the blood vessel detected by the detector are integrated, and numerical value information regarding a substance included in blood of the living body is measured based on an integration result;
    the control unit performs, after the spectrum is detected by the detector, adjustment processing for enlarging the irradiation range and then restoring the irradiation range, or reducing the irradiation intensity and then restoring the irradiation intensity in a case where it is determined that the irradiated position is the blood vessel position in the determination processing by the determination unit;
    the control unit changes the irradiation position in a case where it is determined in the determination processing that the irradiation position is not the blood vessel position, and performs the adjustment processing in a case where it is determined in the determination processing that the irradiation position is the blood vessel position; and
    the detector newly detects the spectrum after the adjustment processing is performed.

6. The blood measuring apparatus according to claim 5, further comprising:
    a calculation unit configured to integrate the plurality of spectra detected by the detector,
    wherein the calculation unit excludes, as an integration target, the spectrum corresponding to the irradiation position determined in the determination processing not to be the blood vessel position.

7. The blood measuring apparatus according to claim 5, wherein
    the living body is irradiated with the excitation light having an irradiation range of a predetermined size and an irradiation intensity of a predetermined magnitude in order to detect the spectrum,
    at least one of a duration for the irradiation range of a predetermined size and a duration for the irradiation intensity of a predetermined magnitude is limited, and a setting of the limited duration can be changed.

* * * * *